(12) United States Patent
Gao et al.

(10) Patent No.: US 10,556,871 B1
(45) Date of Patent: Feb. 11, 2020

(54) METHOD FOR PREPARING 5-(4-BROMOPHENYL)-4,6-DICHLOROPYRIMIDINE

(71) Applicant: ZHEJIANG XIANFENG TECHNOLOGIES CO.,LTD, Zhejiang (CN)

(72) Inventors: Feifei Gao, Zhejiang (CN); Junlong Gao, Zhejiang (CN); Minliang Zhu, Zhejiang (CN); Wei Lu, Zhejiang (CN); Yi Liu, Zhejiang (CN)

(73) Assignee: ZHEJIANG XIANFENG TECHNOLOGIES CO., LTD., Zhejiang (CN)

( * ) Notice: Subject to any disclaimer, the term of this patent is extended or adjusted under 35 U.S.C. 154(b) by 0 days.

(21) Appl. No.: 16/243,091

(22) Filed: Jan. 9, 2019

(30) Foreign Application Priority Data

Aug. 9, 2018 (CN) .......................... 2018 1 0905221

(51) Int. Cl.
*C07D 239/30* (2006.01)
*B01J 21/06* (2006.01)
*B01J 27/053* (2006.01)
*B01J 21/08* (2006.01)
*B01J 23/745* (2006.01)

(52) U.S. Cl.
CPC .......... *C07D 239/30* (2013.01); *B01J 21/063* (2013.01); *B01J 21/066* (2013.01); *B01J 21/08* (2013.01); *B01J 23/745* (2013.01); *B01J 27/053* (2013.01)

(58) Field of Classification Search
CPC .................................................. C07D 239/30
See application file for complete search history.

(56) References Cited

U.S. PATENT DOCUMENTS

| 7,094,781 B2 * | 8/2006 | Bolli | C07D 239/47 514/235.8 |
| 2018/0370954 A1 * | 12/2018 | Jamjanam | C07D 403/12 |

* cited by examiner

*Primary Examiner* — Emily A Bernhardt
(74) *Attorney, Agent, or Firm* — JCIPRNET

(57) ABSTRACT

A method for preparing 5-(4-bromophenyl)-4,6-dichloropyrimidine is provided. The method comprises the steps of: preparing methyl p-bromophenylacetate (Intermediate I) by catalytic esterification of p-bromophenylacetic acid, and then reacting with dimethyl carbonate to synthesize 2-(4-bromophenyl)-malonic acid-1,3-dimethyl ester (Intermediate 2), cyclizing with formamidine hydrochloride to obtain 5-(4-bromophenyl)-4,6-dihydroxypyrimidine (Intermediate 3), and then chlorinating to give the product 5-(4-bromophenyl)-4,6-dichloropyrimidine. In the process of preparing Intermediate 1 in the present invention, a solid acid is used as a catalyst. Moreover, in the process of preparing Intermediate 2, sodium methoxide is used as a base in place of sodium hydride or sodium amide used in the prior art. Furthermore, Intermediate 3 is prepared by a one-pot process.

8 Claims, 1 Drawing Sheet

METHOD FOR PREPARING 5-(4-BROMOPHENYL)-4,6-DICHLOROPYRIMIDINE

CROSS-REFERENCE TO RELATED APPLICATION

This application claims the priority benefit of China application serial no. 201810905221.1, filed on Aug. 9, 2018. The entirety of the above-mentioned patent application is hereby incorporated by reference herein and made a part of this specification.

BACKGROUND

1. Field of the Invention

The present invention relates to the technical field of chemical synthesis of drugs, and to a method for preparing 5-(4-bromophenyl)-4,6-dichloropyrimidine.

2. Description of Related Art

Macitentan is a bi-directional endothelin receptor antagonist developed by Actelion Pharmaceuticals Inc. Macitentan was approved by the FDA on Oct. 18, 2013 under the trade name Opsumit for the treatment of pulmonary arterial hypertension (PAH) to delay the disease progression. Its chemical name is N-[5-(4-bromophenyl)-6-[2-[(5-bromo-2-pyrimidinyl)oxy]ethoxy]-4-pyrimidinyl]-N'-propylsulfamide.

5-(4-bromophenyl)-4,6-dichloropyrimidine (CAS: 146533-41-7) is an important intermediate in the synthesis of Macitentan. The intermediate is synthesized starting with p-bromophenylacetic acid. The first step is an esterification reaction, in which concentrated sulfuric acid or thionyl chloride is frequently used as a catalyst in the prior art, as described in the synthesis method disclosed in Journal of Medicinal Chemistry 55, 7849-7861, 2012. However, use of concentrated sulfuric acid or thionyl chloride as a catalyst causes the disadvantages of complicated process and troublesome post-treatment, and the catalyst is difficult to recycle, leading to waste of resources and increase of production cost.

SUMMARY

According to one aspect of this invention, a method for preparing 5-(4-bromophenyl)-4,6-dichloropyrimidine is provided.

A method for preparing 5-(4-bromophenyl)-4,6-dichloropyrimidine comprises the steps of:

Step 1: adding p-bromophenylacetic acid and a solid acid catalyst to a reactor, then adding methanol, heating with stirring, and refluxing to react for 5-6 hours under reflux; and cooling the reaction solution to 30° C. or below, filtering to recover the solid acid catalyst, distilling the resulting filtrate under reduced pressure to remove methanol, adding a hydrophobic solvent to dissolve the residue by stirring, washing the hydrophobic solvent with water, and concentrating under reduced pressure to obtain Intermediate 1;

Step 2: adding sodium methoxide and methanol to Intermediate 1 obtained in Step 1, mechanically stirring, then adding dimethyl carbonate, replacing the air in the reactor with nitrogen, heating to 70-80° C., and reacting for 4-8 hours, to obtain a mixture containing Intermediate 2;

Step 3: adding formamidine hydrochloride to the mixture containing Intermediate 2 obtained in Step 2, heating to 20-30° C. with stirring, and reacting for 15-17 hours, followed by post-treatment, to obtain Intermediate 3; and Step 4: chlorinating Intermediate 3 obtained in Step 3 to obtain the product 5-(4-bromophenyl)-4,6-dichloropyrimidine. The raw material p-bromophenylacetic acid has a structural formula of:

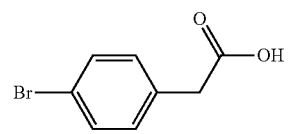 [SMILES: O=C(O)Cc1ccc(Br)cc1]

Intermediate 1 has a structural formula of:

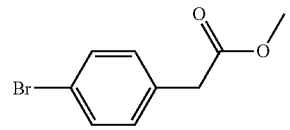

Intermediate 2 has a structural formula of:

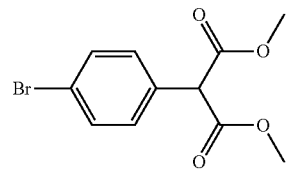 [SMILES: COC(=O)C(C(=O)OC)c1ccc(Br)cc1]

Intermediate 3 has a structural formula of:

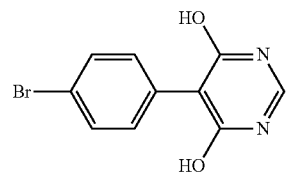 [SMILES: Clc1ncnc(Cl)c1-c1ccc(Br)cc1]

The product 5-(4-bromophenyl)-4,6-dichloropyrimidine has a structural formula of:

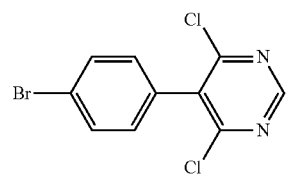

In the method for preparing 5-(4-bromophenyl)-4,6-dichloropyrimidine, the solid acid catalyst in Step 1 is a complex of iron oxide, zirconium oxide, titanium oxide, diatomaceous earth or silica gel with sulfate ions loaded thereon.

In the method for preparing 5-(4-bromophenyl)-4,6-dichloropyrimidine, the hydrophobic solvent in Step 1 is toluene.

In the method for preparing 5-(4-bromophenyl)-4,6-dichloropyrimidine, the weight ratio of p-bromophenylacetic acid to the solid acid catalyst is 1:0.4-0.6; and the weight ratio of methyl p-bromophenylacetate, dimethyl carbonate, sodium methoxide, and formamidine hydrochloride is 1:1.0-1.5:0.6-1.0:0.35-0.55.

In the method for preparing 5-(4-bromophenyl)-4,6-dichloropyrimidine, the post-treatment in Step 3 comprises:

Step (a): adding water to the reaction solution, stirring at 20-30° C. until the reaction solution becomes clear, and standing for layering;

Step (b): collecting the aqueous phase, adjusting to pH 4-6 with an acidic solution, and stirring for 0.5-1.5 hours; and Step (c): filtering under suction, washing the obtained filter cake with an 80 wt % aqueous methanol solution, and drying to obtain Intermediate 3.

In the method for preparing 5-(4-bromophenyl)-4,6-dichloropyrimidine, the acidic solution in Step (b) is a hydrochloric acid solution or a sulfuric acid solution.

In the method for preparing 5-(4-bromophenyl)-4,6-dichloropyrimidine, the chlorination in Step 4 comprises:

Step (I): adding toluene and N,N-dimethyl aniline to Intermediate 3, mechanically stirring, adding phosphorus oxychloride at 20-35° C., heating to 50-60° C. and then to 95-105° C. after the solid is completely dissolved, reacting for 3-5 hours, and then cooling to 20-30° C. for later use;

Step (II): mixing water with toluene, cooling to 20-30° C. with stirring, and adding to the ready-to-use reaction solution obtained in Step (I), during which the temperature is controlled to 25-35° C.;

Step (III): stirring for 0.5-1.5 hours at 25-35° C., standing for layering, extracting the aqueous phase several times with toluene, and combining the toluene extract and organic phase; and Step (IV): removing the solvent from the combined organic phase obtained in Step (III) under reduced pressure, adding ethanol, stirring for 1-2 hours at 10-20° C., filtering under suction, and drying to obtain the product 5-(4-bromophenyl)-4,6-dichloropyrimidine.

In the method for preparing 5-(4-bromophenyl)-4,6-dichloropyrimidine, the chlorination in Step 4 comprises:

Step (1): adding toluene and N,N-dimethylaminopyridine to Intermediate 3, mechanically stirring, adding solid phosgene stepwise at 20-35° C., then increasing the temperature to 95-105° C., reacting for 3-5 hours, and then cooling to 20-30° C. for later use;

Step (2): mixing water with toluene, cooling to 20-30° C. with stirring, and adding the ready-to-use reaction solution obtained in Step (I), during which the temperature is controlled to 25-35° C.;

Step (3): stirring for 0.5-1.5 hours at 25-35° C., standing for layering, extracting the aqueous phase several times with toluene, and combining the toluene extract and the organic phase; and Step (4): removing the solvent from the combined organic phase obtained in Step (3) under reduced pressure, adding ethanol, stirring for 1-2 hours at 10-20° C., filtering under suction, and drying to obtain the product 5-(4-bromophenyl)-4,6-dichloropyrimidine.

The process route of the present invention is as follows:

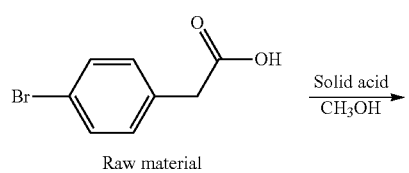

Raw material

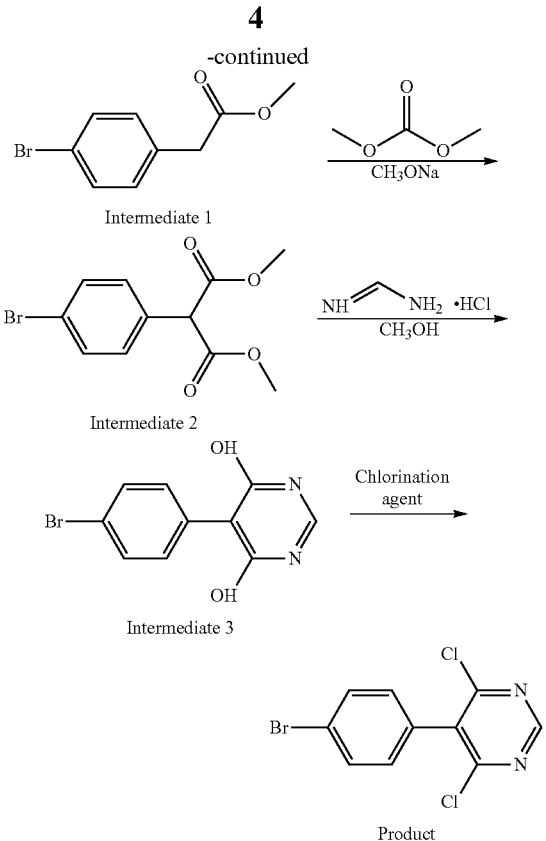

Compared with the prior art, the present invention has the following beneficial effects.

1. In the process of preparing Intermediate 1 in the present invention, a solid acid is used as a catalyst, which simplifies the synthesis process and the post-treatment steps, and the solid acid is easy to be separated, and recyclable, thereby saving resources and reducing the production cost.

2. In the present invention, a one-pot method is employed to prepare Intermediate 2 and Intermediate 3, and the solvent used in both steps of reactions is methanol, which saves the step of solvent change in the reaction system, makes the process simpler, and also improves the conversion rate.

3. In the process of preparing Intermediate 2 in the present invention, sodium methoxide is used as a base in place of sodium hydride or sodium amide used in the prior art, which improves the safety of the reaction and reduces the reaction cost.

4. The total conversion rate of the process route provided by the invention is high, and the obtained 5-(4-bromophenyl)-4,6-dichloropyrimidine has high purity and contains less impurities.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
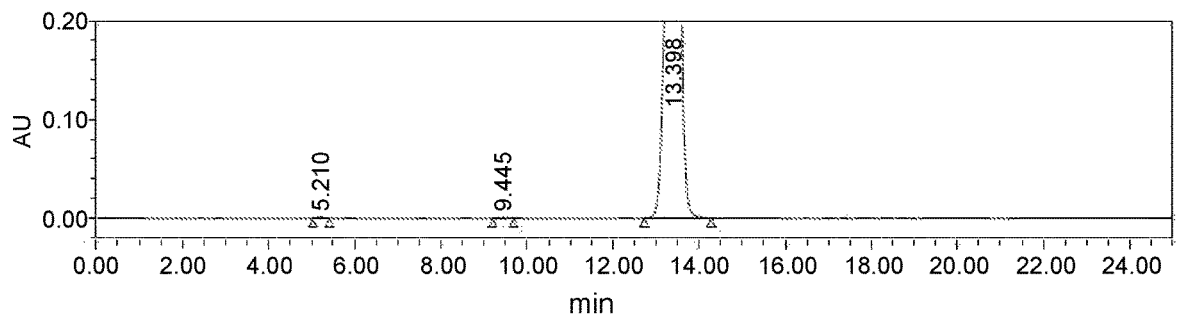
FIG. 1 is a liquid chromatogram of the product obtained in Example 1.

Reference will now be made in detail to the present preferred embodiments of the invention, examples of which are illustrated in the accompanying drawings. Wherever possible, the same reference numbers are used in the drawings and the description to refer to the same or like parts.

Reagents used in the following examples are commercially available, unless otherwise specified.

Example 1

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 200 g of a solid acid catalyst were added. Then, 2.7 L of methanol was added, heated with stirring and reacted under reflux for 5 hours.

The solid acid catalyst may be a complex of iron oxide, zirconium oxide, titanium oxide, diatomaceous earth or silica gel with sulfate ions loaded thereon, and may be purchased from Qufu Shengquan Catalyst Application Technology Co., Ltd. The solid acid catalyst used in examples that follows was the same as that in this example, and thus will not be described there again. The reaction solution was cooled to 20° C. or below, the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure to obtain 501.0 g of Intermediate 1 (yield 94.1%).

Step 2: 250 g of Intermediate 1 obtained in Step 1 was added to a 5 L four-neck flask, then 150 g of sodium methoxide and 1000 g of methanol were added, and mechanically stirred.

Then, 250 g of dimethyl carbonate was added, the air in the reactor was replaced with nitrogen, the temperature was raised to 70° C., and the reaction was continued for 4 hours to obtain a mixture containing Intermediate 2.

Step 3: 87.5 g of formamidine hydrochloride was added to the mixture containing Intermediate 2 obtained in Step 2, heated to 20° C. with stirring, and reacted for 15 hours. Then water was added to the reaction solution, stirred at 20° C. until the solution becomes clear, and stood for layering. The aqueous phase was collected, adjusted to pH 4 with a hydrochloric acid solution, stirred for 0.5 h, and filtered under suction. The resulting filter cake was washed with an 80 wt % aqueous methanol solution, and dried to obtain 268.6 g of Intermediate 3 (yield 92.1%).

Step 4: 200 g of Intermediate 3 obtained in Step 3 was added to a 3 L three-neck flask, and then 300 g of toluene and 180 g of N,N-dimethyl aniline were added, and mechanically stirred. 230 g of phosphorus oxychloride was added dropwise at 20° C., heated to 50° C. and then to 95° C. after the solid was completely dissolved, reacted for 3 hours, and then cooled to 20° C. for later use. 450 g of water was mixed with 500 g of toluene, cooled to 20° C. with stirring, and added to the above ready-to-use reaction solution, during which the temperature was controlled to 25° C. The solution was stirred for 0.5 h at 25° C., and stood for layering. The aqueous phase was extracted several times with toluene, and the toluene extract and the organic phase were combined. The solvent was removed from combined organic phase under reduced pressure, and then ethanol was added. The resulting solution was stirred for 1 hour at 10° C., filtered under suction, and dried to obtain 195.0 g of the product 5-(4-bromophenyl)-4,6-dichloropyrimidine (yield 85.7%). The detection results by liquid chromatography (LC) of the obtained product were shown in FIG. 1.

The purity by HPLC was 99.88%, and the detection results were from Waters 2489-1525 high-performance liquid chromatograph manufactured by Waters.

The total yield of the process route provided by the present invention was calculated to be 74.3% based on the reaction yield of each step.

Example 2

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 300 g of a solid acid catalyst were added. Then, 2.7 L of methanol was added, heated with stirring and reacted under reflux for 6 hours. The reaction solution was cooled to 30° C., the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure, to obtain 499.6 g of Intermediate 1 (yield 93.8%).

Step 2: 250 g of Intermediate 1 obtained in Step 1 was added to a 5 L four-neck flask, then 250 g of sodium methoxide and 1000 g of methanol were added, and mechanically stirred. Then, 375 g of dimethyl carbonate was added, the air in the reactor was replaced with nitrogen, the temperature was raised to 80° C., and the reaction was continued for 8 hours to obtain a mixture containing Intermediate 2.

Step 3: 112.5 g of formamidine hydrochloride was added to the mixture containing Intermediate 2 obtained in Step 2, heated to 30° C. with stirring, and reacted for 17 hours. Then water was added to the reaction solution, stirred at 30° C. until the solution becomes clear, and stood for layering. The aqueous phase was collected, adjusted to pH 6 with a sulfuric acid solution, stirred for 1.5 hours, and filtered under suction. The resulting filter cake was washed with an 80 wt % aqueous methanol solution, and dried to obtain 267.8 g of Intermediate 3 (yield 91.8%).

Step 4: 200 g of Intermediate 3 obtained in Step 3 was added to a 3 L three-neck flask, and then 300 g of toluene and 180 g of N,N-dimethyl aniline were added, and mechanically stirred. 230 g of phosphorus oxychloride was added dropwise at 35° C., heated to 60° C. and then to 105° C. after the solid was completely dissolved, reacted for 5 hours, and then cooled to 30° C. for later use. 450 g of water was mixed with 500 g of toluene, cooled to 30° C. with stirring, and added to the above ready-to-use reaction solution, during which the temperature was controlled to 35° C. The solution was stirred for 1.5 hours at 35° C., and stood for layering. The aqueous phase was extracted several times with toluene, and the toluene extract and the organic phase were combined. The solvent was removed from the combined organic phase under reduced pressure, and then ethanol was added. The resulting solution was stirred for 2 h at 20° C., filtered under suction, and dried to obtain 194.8 g of the product 5-(4-bromophenyl)-4,6-dichloropyrimidine (yield 85.6%).

The total yield of the process route provided by the present invention was calculated to be 73.7% based on the reaction yield of each step.

Example 3

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 250 g of a solid acid catalyst were added. Then, 2.7 L of methanol was added, heated with stirring and reacted under reflux for 5.5 hours. The reaction solution was cooled to 25° C., the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure, to obtain 505.4 g of Intermediate 1 (yield 94.9%).

Step 2: 250 g of Intermediate 1 obtained in Step 1 was added to a 5 L four-neck flask, then 200 g of sodium methoxide and 1000 g of methanol were added, and mechanically stirred. Then, 312.5 g of dimethyl carbonate was added, the air in the reactor was replaced with nitrogen, the temperature was raised to 75° C., and the reaction was continued for 6 hours to obtain a mixture containing Intermediate 2.

Step 3: 100 g of formamidine hydrochloride was added to the mixture containing Intermediate 2 obtained in Step 2, heated to 25° C. with stirring, and reacted for 16 hours. Then water was added to the reaction solution, stirred at 25° C. until the solution becomes clear, and stood for layering. The aqueous phase was collected, adjusted to pH 5 with a hydrochloric acid solution, stirred for 1 hour, and filtered under suction. The resulting filter cake was washed with an 80 wt % aqueous methanol solution, and dried to obtain 270.2 g of Intermediate 3 (yield 92.6%).

Figure 2:
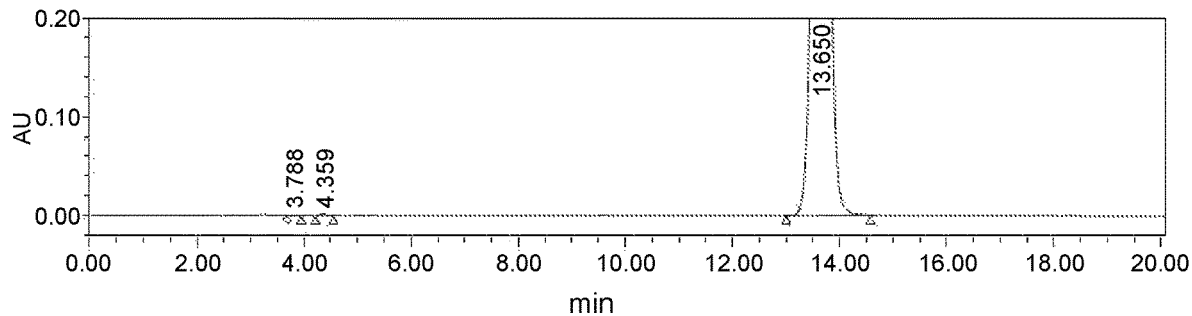
FIG. 2 is a liquid chromatogram of the product obtained in Example 3.

Step 4: 200 g of Intermediate 3 obtained in Step 3 was added to a 3 L three-neck flask, and then 300 g of toluene and 180 g of N,N-dimethyl aniline were added, and mechanically stirred. 230 g of phosphorus oxychloride was added dropwise at 30° C., heated to 55° C. and then to 100° C. after the solid was completely dissolved, reacted for 4 hours, and then cooled to 25° C. for later use. 450 g of water was mixed with 500 g of toluene, cooled to 25° C. with stirring, and added to the above ready-to-use reaction solution, during which the temperature was controlled to 30° C. The solution was stirred for 1 hour at 30° C., and stood for layering. The aqueous phase was extracted several times with toluene, and the toluene extract and the organic phase were combined. The solvent was removed from the combined organic phase under reduced pressure, and then ethanol was added. The resulting solution was stirred for 1.5 hours at 15° C., filtered under suction, and dried to obtain 195.6 g of the product 5-(4-bromophenyl)-4,6-dichloropyrimidine (yield 86.0%). The detection results by LC of the obtained product were as shown in FIG. 2. The purity by HPLC was 99.93%, and the detection results were from Waters 2489-1525 high-performance liquid chromatograph manufactured by Waters.

The total yield of the process route provided by the present invention was calculated to be 75.6% based on the reaction yield of each step.

Example 4

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 200 g of a solid acid catalyst were added. Then, 2.7 L of methanol was added, heated with stirring and reacted under reflux for 5 hours. The reaction solution was cooled to 20° C., the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure, to obtain 501.2 g of Intermediate 1 (yield 94.1%).

Step 2: 250 g of Intermediate 1 obtained in Step 1 was added to a 5 L four-neck flask, then 150 g of sodium methoxide and 1000 g of methanol were added, and mechanically stirred. Then, 250 g of dimethyl carbonate was added, the air in the reactor was replaced with nitrogen, the temperature was raised to 70° C., and the reaction was continued for 4 hours to obtain a mixture containing Intermediate 2.

Step 3: 87.5 g of formamidine hydrochloride was added to the mixture containing Intermediate 2 obtained in Step 2, heated to 20° C. with stirring, and reacted for 15 hours. Then water was added to the reaction solution, stirred at 20° C. until the solution becomes clear, and stood for layering. The aqueous phase was collected, adjusted to pH 4 with a hydrochloric acid solution, stirred for 0.5 hr, and filtered under suction. The resulting filter cake was washed with an 80 wt % aqueous methanol solution, and dried to obtain 268.2 g of Intermediate 3 (yield 92.0%).

Step 4: 200 g of Intermediate 3 obtained in Step 3 was added to a 3 L three-neck flask, and then 300 g of toluene and 5 g of N,N-dimethylaminopyridine were added, and mechanically stirred. 520 g of solid phosgene was added stepwise at 20° C., then heated to 95° C., reacted for 3 hours, and then cooled to 20° C. for later use. 450 g of water was mixed with 500 g of toluene, cooled to 20° C. with stirring, and added to the above ready-to-use reaction solution, during which the temperature was controlled to 25° C. The solution was stirred for 0.5 h at 25° C., and stood for layering. The aqueous phase was extracted several times with toluene, and the toluene extract and the organic phase were combined. The solvent was removed from the combined organic phase under reduced pressure, and then ethanol was added. The resulting solution was stirred for 1 hour at 10° C., filtered under suction, and dried to obtain 192.2 g of the product 5-(4-bromophenyl)-4,6-dichloropyrimidine (yield 84.5%).

The total yield of the process route provided by the present invention was calculated to be 73.2% based on the reaction yield of each step.

Example 5

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 300 g of a solid acid catalyst were added. Then, 2.7 L of methanol was added, heated with stirring and reacted under reflux for 6 hours. The reaction solution was cooled to 30° C., the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure, to obtain 499.9 g of Intermediate 1 (yield 93.9%).

Step 2: 250 g of Intermediate 1 obtained in Step 1 was added to a 5 L four-neck flask, then 250 g of sodium methoxide and 1000 g of methanol were added, and mechanically stirred. Then, 375 g of dimethyl carbonate was added, the air in the reactor was replaced with nitrogen, the temperature was raised to 80° C., and the reaction was continued for 8 hours to obtain a mixture containing Intermediate 2.

Step 3: 112.5 g of formamidine hydrochloride was added to the mixture containing Intermediate 2 obtained in Step 2, heated to 30° C. with stirring, and reacted for 17 hours. Then water was added to the reaction solution, stirred at 30° C. until the solution becomes clear, and stood for layering. The aqueous phase was collected, adjusted to pH 6 with a sulfuric acid solution, stirred for 1.5 hours, and filtered under suction. The resulting filter cake was washed with an 80 wt % aqueous methanol solution, and dried to obtain 267.6 g of Intermediate 3 (yield 91.8%).

Step 4: 200 g of Intermediate 3 obtained in Step 3 was added to a 3 L three-neck flask, and then 300 g of toluene and 5 g of N,N-dimethylaminopyridine were added, and mechanically stirred. 520 g of solid phosgene was added stepwise at 35° C., then heated to 105° C., reacted for 5 hours, and then cooled to 30° C. for later use. 450 g of water was mixed with 500 g of toluene, cooled to 30° C. with stirring, and added to the above ready-to-use reaction solution, during which the temperature was controlled to 35° C. The solution was stirred for 1.5 hours at 35° C., and stood for layering. The aqueous phase was extracted several times with toluene, and the toluene extract and the organic phase were combined. The solvent was removed from the combined organic phase under reduced pressure, and then ethanol was added. The resulting solution was stirred for 2 h at 20° C., filtered under suction, and dried to obtain 192.1 g of the product 5-(4-bromophenyl)-4,6-dichloropyrimidine (yield 84.5%).

The total yield of the process route provided by the present invention was calculated to be 72.8% based on the reaction yield of each step.

Example 6

In this embodiment, a method for preparing 5-(4-bromophenyl)-4,6-dichloropyrimidine is provided, which comprises the following steps, specifically.

Step 1: To a 5.0 L reaction flask, 500 g of p-bromophenylacetic acid and 250 g of a solid acid catalyst were added. Then, 2.7 L of methanol was added, heated with stirring and reacted under reflux for 5.5 hours. The reaction solution was cooled to 25° C., the solid acid catalyst was recovered by filtering, and the resulting filtrate was distilled under reduced pressure to remove methanol. 2.0 L of toluene was added to dissolve the residue by stirring, and the toluene was washed with water, and concentrated under reduced pressure, to obtain 505.6 g of Intermediate 1 (yield 95.0%).

Step 2: 250 g of Intermediate 1 obtained in Step 1 was added to a 5 L four-neck flask, then 200 g of sodium methoxide and 1000 g of methanol were added, and mechanically stirred. Then, 312.5 g of dimethyl carbonate was added, the air in the reactor was replaced with nitrogen, the temperature was raised to 75° C., and the reaction was continued for 6 hours to obtain a mixture containing Intermediate 2.

Step 3: 100 g of formamidine hydrochloride was added to the mixture containing Intermediate 2 obtained in Step 2, heated to 25° C. with stirring, and reacted for 16 hours. Then water was added to the reaction solution, stirred at 25° C. until the solution becomes clear, and stood for layering. The aqueous phase was collected, adjusted to pH 5 with a hydrochloric acid solution, stirred for 1 hour, and filtered under suction. The resulting filter cake was washed with an 80 wt % aqueous methanol solution, and dried to obtain 269.7 g of Intermediate 3 (yield 92.5%).

Figure 3:
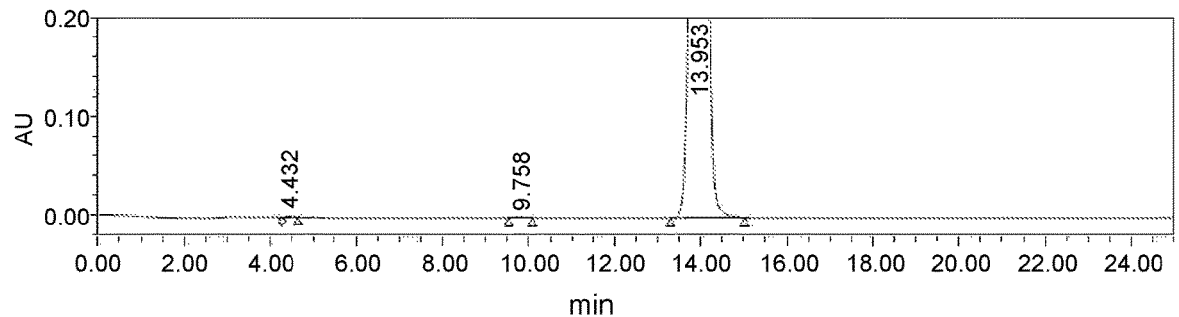
FIG. 3 is a liquid chromatogram of the product obtained in Example 6.

Step 4: 200 g of Intermediate 3 obtained in Step 3 was added to a 3 L three-neck flask, and then 300 g of toluene and 5 g of N,N-dimethylaminopyridine were added, and mechanically stirred. 520 g of solid phosgene was added stepwise at 30° C., heated to 100° C., reacted for 4 hours, and then cooled to 25° C. for later use. 450 g of water was mixed with 500 g of toluene, cooled to 25° C. with stirring, and added to the above ready-to-use reaction solution, during which the temperature was controlled to 30° C. The solution was stirred for 1 hour at 30° C., and stood for layering. The aqueous phase was extracted several times with toluene, and the toluene extract and the organic phase were combined. The solvent was removed from the combined organic phase under reduced pressure, and then ethanol was added. The resulting solution was stirred for 1.5 hours at 15° C., filtered under suction, and dried to obtain 192.5 g of the product 5-(4-bromophenyl)-4,6-dichloropyrimidine (yield 84.6%). The detection results by LC of the obtained product were as shown in FIG. 3. The purity by HPLC was 99.93%, and the detection results were from Waters 2489-1525 high-performance liquid chromatograph manufactured by Waters.

The total yield of the process route provided by the present invention was calculated to be 74.3% based on the reaction yield of each step.

The specific embodiments described herein are merely illustrative of the spirit of the invention. Various modifications, supplements, or similar replacements can be made to the specific embodiments described by those skilled in the art without departing from the spirit or going beyond the scope as defined by the appended claims of the present invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for preparing 5-(4-bromophenyl)-4,6-dichloropyrimidine, comprising:

Step 1: adding p-bromophenylacetic acid and a solid acid catalyst to a reactor, then adding methanol, heating with stirring, and refluxing to react for 5-6 hours under reflux; and cooling the reaction solution to 30° C. or below, filtering to recover the solid acid catalyst, distilling the resulting filtrate under reduced pressure to remove methanol, adding a hydrophobic solvent to dissolve the residue by stirring, washing the hydrophobic solvent with water, and concentrating under reduced pressure to obtain Intermediate 1 having a chemical structure (I) below;

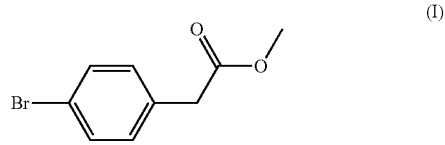

Step 2: adding sodium methoxide and methanol to Intermediate 1 obtained in Step 1, mechanically stirring, then adding dimethyl carbonate, replacing the air in the reactor with nitrogen, heating to 70-80° C., and reacting for 4-8 hours, to obtain a mixture containing Intermediate 2 having a chemical structure (II) below;

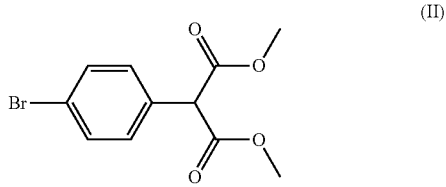 [SMILES: COC(=O)C(C(=O)OC)c1ccc(Br)cc1]

(II)

Step 3: adding formamidine hydrochloride to the mixture containing Intermediate 2 obtained in Step 2, heating to 20-30° C. with stirring, and reacting for 15-17 hours, followed by post-treatment, to obtain Intermediate 3 having a chemical structure (III) below; and

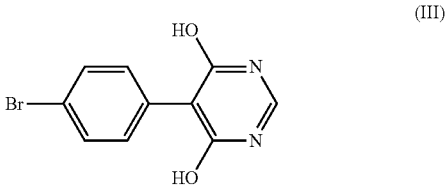 [SMILES: Oc1ncnc(O)c1-c1ccc(Br)cc1]

(III)

Step 4: chlorinating Intermediate 3 obtained in Step 3 to obtain the product 5-(4-bromophenyl)-4,6-dichloropyrimidine.

2. The method for preparing 5-(4-bromophenyl)-4,6-dichloropyrimidine according to claim 1, wherein the solid acid catalyst in Step 1 is a complex of iron oxide, zirconium oxide, titanium oxide, diatomaceous earth or silica gel with sulfate ions loaded thereon.

3. The method for preparing 5-(4-bromophenyl)-4,6-dichloropyrimidine according to claim 1, wherein the hydrophobic solvent in Step 1 is toluene.

4. The method for preparing 5-(4-bromophenyl)-4,6-dichloropyrimidine according to claim 1, wherein the weight ratio of p-bromophenylacetic acid to the solid acid catalyst is 1:0.4-0.6; Intermediate 1 is methyl p-bromophenylacetate; and the weight ratio of methyl p-bromophenylacetate, dimethyl carbonate, sodium methoxide, and formamidine hydrochloride is 1:1.0-1.5:0.6-1.0:0.35-0.55.

5. The method for preparing 5-(4-bromophenyl)-4,6-dichloropyrimidine according to claim 1, wherein the post-treatment in Step 3 comprises:
Step (a): adding water to the reaction solution, stirring at 20-30° C. until the reaction solution becomes clear, and standing for layering;
Step (b): collecting the aqueous phase, adjusting to pH 4-6 with an acidic solution, and stirring for 0.5-1.5 hours; and
Step (c): filtering under suction, washing the obtained filter cake with an 80 wt % aqueous methanol solution, and drying to obtain Intermediate 3.

6. The method for preparing 5-(4-bromophenyl)-4,6-dichloropyrimidine according to claim 5, wherein the acidic solution in Step (b) is a hydrochloric acid solution or a sulfuric acid solution.

7. The method for preparing 5-(4-bromophenyl)-4,6-dichloropyrimidine according to claim 1, wherein the chlorination in Step 4 comprises:
Step (I): adding toluene and N,N-dimethyl aniline to Intermediate 3, mechanically stirring, adding phosphorus oxychloride at 20-35° C., heating to 50-60° C. and then to 95-105° C. after the solid is completely dissolved, reacting for 3-5 hours, and then cooling to 20-30° C. for later use;
Step (II): mixing water with toluene, cooling to 20-30° C. with stirring, and adding to the ready-to-use reaction solution obtained in Step (I), during which the temperature is controlled to 25-35° C.;
Step (III): stirring for 0.5-1.5 hours at 25-35° C., standing for layering, extracting the aqueous phase several times with toluene, and combining the toluene extract and the organic phase; and
Step (IV): removing the solvent from the combined organic phase obtained in Step (III) under reduced pressure, adding ethanol, stirring for 1-2 hours at 10-20° C., filtering under suction, and drying to obtain the product 5-(4-bromophenyl)-4,6-dichloropyrimidine.

8. The method for preparing 5-(4-bromophenyl)-4,6-dichloropyrimidine according to claim 1, wherein the chlorination in Step 4 comprises:
Step (1): adding toluene and N,N-dimethylaminopyridine to Intermediate 3, mechanically stirring, adding solid phosgene stepwise at 20-35° C., then increasing temperature to 95-105° C., reacting for 3-5 hours, and then cooling to 20-30° C. for later use;
Step (2): mixing water with toluene, cooling to 20-30° C. with stirring, and adding to the ready-to-use reaction solution obtained in Step (I), during which the temperature is controlled to 25-35° C.;
Step (3): stirring for 0.5-1.5 hours at 25-35° C., standing for layering, extracting the aqueous phase several times with toluene, and combining the toluene extract and the organic phase; and
Step (4): removing the solvent from the combined organic phase obtained in Step (3) under reduced pressure, adding ethanol, stirring for 1-2 hours at 10-20° C., filtering under suction, and drying to obtain the product 5-(4-bromophenyl)-4,6-dichloropyrimidine.

* * * * *